United States Patent [19]

DesMarteau

[11] Patent Number: 4,697,011
[45] Date of Patent: Sep. 29, 1987

[54] N-FLUORO-N-PERFLUOROMETHYL SULFONAMIDES

[75] Inventor: Darryl D. DesMarteau, Clemson, S.C.

[73] Assignee: Research Corporation, New York, N.Y.

[21] Appl. No.: 889,034

[22] Filed: Jul. 18, 1986

Related U.S. Application Data

[63] Continuation-in-part of Ser. No. 758,604, Jul. 24, 1985.
[51] Int. Cl.$^4$ .................. C07C 143/72; C07C 143/74
[52] U.S. Cl. .................................. 540/544; 548/123; 548/951; 544/5; 564/82; 564/96; 564/97
[58] Field of Search ........................... 564/96, 97, 82; 540/544; 548/951, 123; 544/5

[56] References Cited

U.S. PATENT DOCUMENTS 3,917,688 11/1975 Barton et al. .
4,387,222 6/1983 Koshar .
4,387,222 6/1983 Koshar .
4,429,093 1/1984 Koshar .
4,479,901 10/1984 Barnette .

FOREIGN PATENT DOCUMENTS 1437074 5/1976 United Kingdom .

OTHER PUBLICATIONS

Rosen et al, *J. Org. Chem.*, 51, (1986), pp. 3607–3611.
Krespan et al, *J. Org. Chem.*, 51, (1986), pp. 4460–4466.
J. Foropoulos et al, Inorganic Chemistry, Nov. 7, 1984, vol. 23 pp. 3720–3723.
D. H. R. Barton et al., J.C.S. Perkin I, 1974, pp. 732–738.
Chemiker Zeitung, 1972, vol. 96, p. 582–Meussdoerffer et al.
R. D. Trepka et al. J. Org. Chem., vol. 39, No. 8, 1974, pp. 1094–1098, Acidities and Partition Coefficients of Fluoromethanesulfonamides.
J. Kollonitsh, Israel J. Chem., vol. 17, 1978, pp. 53–59, Novel Methods for Selective Fluorination of Organic Compounds, etc.
Chava Gal, et al., Tetrahedron Letters, vol. 21, 1980, pp. 5067–5070, Selective Fluorination on Tertiary Carbon-Hydrogen Single Bonds, etc.
Ori Lerman et al., J. Org. Chem, 1981, vol. 46, pp. 4629–4631; Acetyl Hypofluoride as a Taming Carrier of Elemental Fluorine etc.
M. C. Gerstenberger et al. Angew. Chem. Int. Ed. Engl. vol. 20, 1981, pp. 647–667; Methods of Fluorination in Organic Chemistry.
S. Stavber et al.; J. Chem. Soc., Chem Commun. 1983, pp. 563–564, Room Temperature Reactions of CsSO$_4$F with Organic Molecules.
Ori Lerman et al.; J. Org. Chem., 1983, vol. 48, pp. 724–727; Acetyl Hypofluoride, a New Moderating Carrier of Elemental Fluorine etc.

*Primary Examiner*—Charles F. Warren
*Assistant Examiner*—Elizabeth A. Flaherty
*Attorney, Agent, or Firm*—Scully, Scott, Murphy & Presser

[57] ABSTRACT

N-fluoro-N-perfluoromethyl sulfonamide compounds are provided as fluorinating agents for the fluorination of organic compounds by either the direct electrophilic fluorination of organic compounds or by the fluorination of organic compound carbanions.

16 Claims, No Drawings

N-FLUORO-N-PERFLUOROMETHYL SULFONAMIDES

CROSS-REFERENCE TO RELATED PATENT APPLICATIONS

This patent application is a continuation-in-part of application Ser. No. 758,604 filed Jul. 24, 1985.

FIELD OF THE INVENTION

The invention relates to certain novel N-fluoro-N-perfluoromethylsulfonamide compounds and to their use as fluorinating agents for the fluorination of organic compounds, and to the preparation of such fluorinating agents.

DESCRIPTION OF THE PRIOR ART

U.S. Pat. No. 4,479,901 and J. Amer. Chem. Soc., Vol. 106, No. 2, pages 452–454, 1984, disclose the use of certain N-fluoro-N-alkyl sulfonamides as fluorinating agents for the fluorination of certain organic carbanions. These fluorinating agents are used by first generating the carbanion of certain organic compounds with a base, followed by the addition of the N-fluoro-N-alkyl sulfonamide. These fluorinating agents are thus not adapted to directly fluorinate organic substrates, such as aromatic compounds. The use of toluene and/or benzene, for example, as solvents, in the fluorination reactions disclosed in these publications indicates that these N-fluoro-N-alkyl sulfonamides are not readily reactable, directly, with aromatic substrates such as toluene or benzene.

Prior to the present invention it has not been readily possible to directly fluorinate organic compounds in high yields with sulfonamide containing fluorinating agents.

OBJECTS OF THE PRESENT INVENTION

An object of the present invention is to provide novel fluorinating agents and processes for the use thereof.

A further object of the present invention is to provide fluorinating agents which may be used to directly fluorinate various organic compounds.

A further object of the present invention is to provide fluorinating agents which may also be useful in the fluorination of organic carbanions.

A still further object of the present invention is to provide fluorinating agents which may be used to fluorinate organic compounds in relatively high yields.

A still further object of the present invention is to provide fluorinating agents which may be used in bulk fluorination reactions.

A still further object of the present invention is to provide a fluorinating agent that is relatively safe to use, and under relatively mild conditions.

A still further object of the present invention is to provide a process for preparing such novel fluorinating agents.

SUMMARY OF THE PRESENT INVENTION

It has now been found, according to the present invention that these and other objects of the present invention may be readily achieved by the use, as disclosed herein, for the fluorination of organic compounds of N-fluoro-N-perfluoromethyl sulfonamide compounds having the formulae I, II, III and IV as follows:

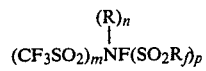
                         I wherein R is a substituted or unsubstituted $C_{1-30}$ branched or straight chain alkyl, $C_{3-30}$ cycloalkyl, aryl ($C_{1-10}$ alkyl) or aryl hydrocarbon group wherein aryl and aryl are $C_{6-14}$ arylene, $R_f$ is a perfluorinated radical which is a $C_{2-30}$ branched or straight chain alkyl, $C_{3-30}$ cycloalkyl, or aryl ($C_{1-10}$ alkyl) or aryl group wherein aryl and aryl are $C_{4-14}$ arylene, m is 1 or 2, n is 0 or 1, p is 0 or 1 and m+n+p=2,

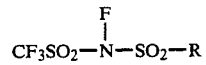
                         II wherein R is as defined above, and

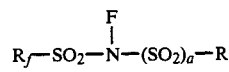
                       III wherein $R_f$ and R are as defined above, and a is 0 or 1, and

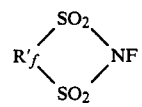
                       IV wherein $R'_f$ is a perfluorinated radical which has the structure $(CF_2)_{n'}$ wherein n' is 1 to 4.

Such formula I compounds include those having the following two formulae:

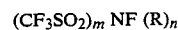
                      IA and

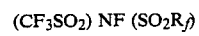
                      IB

Such formula IV compounds include those having the formulae

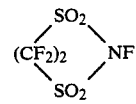
                      IVA which is perfluoro-1,3-dithiazolidine-1,1,3,3-tetraoxide and

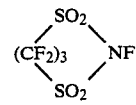
                      IVB which is 2,4,4,5,5,6,6,-heptafluoro-dihydro-1,3,2-dithiazine-1,1,3,3,-tetraoxide.

The term "cycloalkyl" as used herein relative to the definition of the R groups, is intended to include bicycloalkyl groups, for example, 2-norbornyl.

The R groups may be hydrocarbon groups, i.e., unsubstituted, or they may be substituted with one or more groups that are not subject to attack, either, by the fluorinating agent used to make the formulae I to IV compounds, under the conditions used to make such formulae I to IV compounds, or by the NF group of the formula I to IV compounds during the manufacture or use, as fluorinating agents, of the formula I to IV compounds. The substituents that may be employed in this regard would include F, Cl, alkoxy, cyano, nitro, ester, ketol, alkyl sulfonyl (R"SO$_2$—), sulfonyl fluoride (FSO2—), dialkyl amino (R"$_2$N—), amido

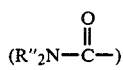

groups, and other such groups, wherein R" is the same as R. The preferred of such R groups are the unsubstituted, or selectively halogenated (with F and/or Cl), alkyl groups.

The preferred of such perfluoromethyl sulfonamide compounds are those formula IA compounds in which m is 2 and n is 0, i.e., N-fluoro-bis(trifluoromethane sulfonyl) imide which has the formula (CF$_3$SO$_2$)$_2$ NF      V and those formula IA compounds in which m is 1, n is 1, and R is CH$_3$, i.e., N-fluoro-N-methyl-trifluoromethane sulfonyl amide which has the formula (CF$_3$SO$_2$)N(F)(CH$_3$)      VI The preferred of such perfluoromethyl sulfonamide compounds of formula IB are those having the formula:

(CF$_3$SO$_2$) NF (SO$_2$R$_f$)      VII

Specific compounds of the present invention having formula VII would include (CF$_3$SO$_2$) NF (SO$_2$C$_4$F$_9$)      VIII and (CF$_3$SO$_2$) NF (SO$_2$C$_6$F$_{13}$)      IX The N-fluoro-N-perfluoromethyl sulfonamide compounds of the present invention i.e., those with formulae I to IV, are prepared by fluoinating compounds having the formulae X, XI, XII, and XIII, respectively, i.e.,

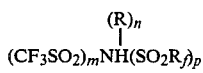      X

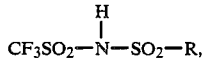      XI

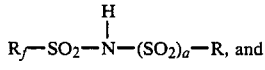      XII

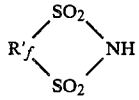      XIII wherein R, R$_f$, R'$_f$, m, n, n', p and a are as defined above.

The preferred formula XIII compounds are those having the formula

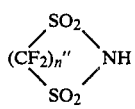      XIIIA where n" is 2 or 3. Where n" is 2 the compound has formula XIIIB, and where n" is 3 the compound has formula XIIIC.

The X formula compounds wherein n and p are 0 may be analogously prepared by the procedures otherwise disclosed by J. Foropoulos and D. D. DesMarteau, Inorg. Chem. 1984, Vol. 23, page 3720.

The X formula compounds wherein n is 1 and p is 0 may be analogously prepared by the procedures otherwise disclosed by R. D. Trepka, J. K. Harrington and J. W. Belisle, J. Org. Chem., 1974, Vol. 39, page 1094 and by J. N. Meussdorffer and H. Niederprum, Chem. Ztg, 1972, Vol. 96, page 582.

The X formula compounds wherein n is 0 and p is 1 may be prepared by the procedures disclosed by J. N. Meussdorffer et al. supra.

The XI and XII compounds can be made by methods, and with reagents, analogous to those employed by J. Foropoulos and D. D. DesMarteau, supra, and by J. N. Meussdorffer and H. Niederprum, supra.

The XIII compounds can be made by reacting a compound of the structure:

FSO$_2$R'$_f$SO$_2$F (wherein R'$_f$ is as defined above) with ammonia in diethyl ether at −20° to −25° C. to directly produce a cyclic ammonium salt having the structure

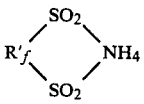      XIIID

Compound XIIID is then reacted with NaOH to produce the sodium salt, stoichiometrically, in an aqueous system. The sodium salt is then reacted with concentrated sulfuric acid to produce compound XIII. Compound XIII is then removed from the excess sulfuric acid by vacuum distillation at 40° C. All of these reactions can be conducted at room temperature (20°-25° C.). These procedures are related to those used by J. Foropoulos and D. D. DesMarteau, supra, and by J. N. Meussdorffer and H. Niederprum supra.

The fluorinating reagents used in the fluorination of the X to XIII formulae compounds would include fluorine gas, alone, or in combination with a metal fluoride such as sodium fluoride; fluoroxy compounds such as CF$_3$OF, and other known fluorinating compounds.

The fluorination of the X to XIII formulae compounds may be conducted at a temperature of about −80° to 22° C., in bulk or in an inert solvent, and under anhydrous conditions, and under autogeneous pressure. When the fluorinating reaction is conducted under flow reaction conditions the fluorinating agent may be diluted with an inert gas such as helium, argon or nitrogen. In a static reaction conducted under autogenous pressure, such as in the preparation of (CF$_3$SO$_2$)$_2$NF as disclosed below, an inert atmosphere is not required. An inert gas may be used to moderate the speed of the reaction, particularly under relatively large scale reaction conditions. The inert solvents would include monofluoro trichloro methane, dichloro difluoro methane, 1,1,2-trichloro trifluoro ethane, dichloro methane, difluoro monochloro methane, chloroform, chloroform-d, and mixtures of such solvents.

The VII formula compounds may also be prepared, it is believed, by the electrochemical fluorination (ECF)

of the corresponding acid, or N-H compound, in hydrofluoric acid, although in somewhat lower yields than may be possible by the other processes disclosed above. Such an ECF reaction is conducted at a temperature of about 0° to −20° C., under anhydrous conditions.

The desired fluorination agents of the present invention may be recovered from the reaction system in which they are prepared by vacuum fractionation. For the preferred formula IA compounds this may be done at low temperatures, of −10° to −196° C. $(CF_3SO_2)_2NF$ and $(CF_3SO_2)N(F)(CH_3)$ are preferably recovered in a fraction collectable at −75°±5° C.

The compounds of formula VII are preferably recovered in a fraction collectable at −40°±20° C. The temperature to be employed in the fractionation of the formula VII compounds will vary over a relatively large range depending on the size of the $R_f$ group in such compounds. The larger is such group, the higher will be the minimum temperature needed to retain the desired compound in the trap.

The compounds of formula IV are preferably recovered in a fraction collectable at −40°±10° C.

The fluorinating compounds of the present invention may be used in two basically different types of fluorination reactions. They may be used to fluorinate organic carbanions in the type of fluorination reactions disclosed in U.S. Pat. No. 4,479,901 and J. Amer. Chem. Soc. Vol. 106, No. 2, pages 452–454, 1984, and they may also be used to directly fluorinate aromatic and other aromatic-like organic compound protons.

The fluorinating reagents used in U.S. Pat. No.4,479,901 and in the JACS publication, supra, cannot readily be used to directly fluorinate organic compound protons. To be readily fluorinated with such reagents, the organic compound in question must first be changed to anion form.

The fluorinating agents of the present invention can be thus used in to either directly fluorinate organic compound protons, or the reagent can be used to fluorinate an organic compound in carbanion form. When used as direct fluorination reagents they are preferably used as so-called electrophilic fluorination reagents. When so used they are particularly useful in the direct fluorination of ring carbon atoms of aromatic compounds that have been activated, relative to the activity of benzene, for such electrophilic reactions. Unsubstituted aromatic compounds such as benzene, naphthalene and anthracene are active enough to be used in such reactions. The presence of activating groups on the aromatic ring will further activate the resulting compounds towards favoring reaction with these electrophilic fluorination reagents.

Such activating groups, on an aromatic ring, would thus include $C_1$ to $C_6$ alkyl groups such as methyl, ethyl, propyl, isopropyl, pentyl and hexyl groups; $C_1$ to $C_6$ alkoxy groups such as methoxy, ethoxy, propoxy, isopropoxy and pentoxy; cycloalkyl groups such as cyclopropyl; aryl groups such as phenyl, and other groups which contain an unshared pair of electrons on the atom connected to the aromatic ring, such as, $NR'_2$, $NHR'$, $NH_2$, $OH$, $NHC(O)R'$, $OC(O)R'$, $SR'$ and halogen (F, Cl, Br and I). $R'$, in such cases, is typically a lower, $C_1$ to $C_4$ alkyl group such as methyl, ethyl, propyl and butyl.

Aromatic ring substituents which have a deactivating effect, so to speak, on the resulting substituted compound, for electrophilic fluorination reaction purposes, are groups which lack an unshared pair of electrons on the atom connected to the aromatic ring, such as nitro ($NO_2$), cyano (CN), sulfonate ($SO_3H$), acyl (C(O)R), $CCl_3$, $NR'_3{}^+$ and other similarly related groups.

When used to directly fluorinate various organic compounds in electrophillic reactions excess amounts of the organic compound can be used as a solvent for the reaction, and the reaction can thus be conducted in bulk. Such reactions can thus be conducted when fluorinating, with the fluorinating reagents of the present invention, aromatic compounds such as benzene, toluene, naphthalene, anisole, phenol, a cresol, i.e., m-cresol and p-cresol, and 1,3.5(10) estratrien-3ol-17one methyl ether.

The electrophilic fluorination type reactions are conducted with the fluorination reagents of the present invention at temperatures of about −80° to 22° C., and preferably of about −10° to 22° C., under anhydrous conditions.

When not conducted in bulk, the electrophilic fluorination reaction is conducted in a solvent inert to the fluorinating agent and to the compound to be fluorinated and the desired resulting products. Such solvents would include carbon tetrachloride, trichloro-monofluoro-methane, dichloro methane, alkanes such as pentane and hexane, chloroform, chloroform-d and deactivated aromatic compounds such as nitrobenzene.

When used in the electrophilic type fluorination reactions the fluorinating agents of the present invention can provide relatively high yields, of the order of up to 80 to 95% or more, depending on the compound being fluorinated.

The fluorinating agents of the present invention, as noted above, may also be used to fluorinate organic compound carbanions, and as otherwise disclosed in U.S. Pat. No. 4,479,901 and the JACS publication mentioned above and except as may be otherwise disclosed herein. Thus, when so used, the organic compound to be fluorinated must first be placed in carbanion form as disclosed in such prior art publications. The types of organic compounds to be so treated with the fluorinating agents of the present invention, in carbanion form, include all those disclosed in such prior art publications. Such organic compounds, in carbanion form, would include dialkyl-1-phenylmalonates and dialkyl-1-alkyl malonates wherein the alkyl groups are lower $C_1$ to $C_4$ alkyl groups. The fluorination of the organic compound carbanions with the fluorinating agents of the present invention can also be conducted as otherwise disclosed in such prior art publications, provided that the reaction is conducted in an inert solvent. Aromatic solvents, for example, such as benzene and toluene, which are inert to the N-fluoro-N-alkylsulfonamide reagents of such prior art publications, and can be used as solvents in the processes of such publications, are not, as noted above, inert to the fluorinating reagents of the present invention at temperatures in the range of about 0 to 40° C. and thus cannot be used as solvents when fluorinating other compounds in carbanion form under such temperature conditions. However, at relatively low temperatures, preferably of the order of about −78°±10° C., such aromatic solvents, where liquid, might be useful, as solvents, in the fluorination of carbanions where an easily fluorinated carbanion can be generated in such solvent at such low temperatures and where the fluorinating reagent of the present invention would preferably react more rapidly with such carbanion, rather than with the solvent.

The contents of U.S. Pat. No. 4,479,901 and the JACS publication are thus incorporated herein by reference with respect to the description therein of the types of organic carbanion compounds (and preparation thereof) that may be used with the fluorinating reagents of the present invention, and the reaction conditions that may be used therewith, subject to the use of inert solvents therewith. The following examples are merely illustrative of the present invention and are not intended as a limitation upon the scope thereof.

EXAMPLE 1

Preparation of N-fluoro-bis(trifluoromethylsulfonyl) Imide, $(CF_3SO_2)_2NF$

Bis(trifluoromethyl sulfonyl) imide, $(CF_3SO_2)_2NH$ (6.0 g, 21.4 mmol) was added to a 300 ml stainless steel bomb in a glove box. The bomb was then cooled to $-20°$ C. and evacuated for 0.5 hour. It was then cooled to $-196°$ C. and fluorine (24.0 mmol) was added by vacuum transfer The bomb was then allowed to warm in the room air to 22° C. and let stand for 24 hours, at which point it was recooled to $-196°$ C. and evacuated to remove unreacted fluorine and any other materials volatile at $-196°$ C. The contents of the bomb were then vacuum transferred to another stainless steel reactor containing sodium fluoride (25 g) and the mixture was allowed to stand at 22° C. for 2 hours, followed by fractionation through a series of three cold traps operated at $-10°$, $-75°$ and $-196°$, C., respectively. The $-196°$ C. trap collected a small amount of $NF_3$ and $CF_3SO_2F$, the $-10°$ C. trap retained a very small amount of unreacted $(CF_2SO_2)_2 NH$, and the $-75°$ C. trap retained pure FN $(SO_2CF_3)_2$ (20.2 mmol, 94.6% yield).

$(CF_3SO_2)_2NF$ is a colorless liquid at 22° C., which forms a crystalline solid on cooling with a melting point of 69.8° C. The compound is stable indefinitely at 22° C. and it is not explosive when the liquid, sealed in a capillary tube, is impacted with a hammer. The vapor pressure of the compound at 25° C. is about 40 torr. The infrared spectrum of the gas at 10 torr shows bonds at 1471(s), 1338(w), 1236(s), 1135(s), 862(s), 770(w), 685(vw), 658(w), 599(s) and 501(m) cm. The $^{19}F$ NMR exhibits two singlets at $-33.7$ (N-F) and $-74.4$ ($CF_3$) ppm relative to internal $CFCl_3$ reference. The areas of the peaks are 1 to 6 as expected for $FN(SO_2CF_3)_2$. The mass spectrum shows an intense parent ion under CI with methane at 300 amu (MH+). The EI spectrum shows intense peaks at 69 ($CF_3^+$) and 133 ($CF_3SO_2^+$). The gas density molecular weight of the compound was 298 (calculated: 299.14).

EXAMPLE 2

Preparation of N-Fluoro-N-methyl-trifluoromethane-sulfonylamide, $CF_3SO_2N(F)CH_3$ N-methyl-trifluoromethansulfonylamide, $CF_3SO_2N(H)CH_3$, (6.0 g, 36.8 mmol) was added to 400 ml of $CFCl_3$ contained in a Teflon reactor. The reactor contained 10 g of NaF, a magnetic stir bar, and a glass fritted inlet below the surface of the solution and an outlet tube The reactor was cooled with stirring to $-75°$ C. while bubbling $N_2$ through the solution. Fluorire gas was then added to the $N_2$ in a concentration of 1 % at a total flow rate of about 440 sccm. This gas mixture was passed through the solution for about 5 hours until a 20% excess of fluorine had been added (about 44 mmol). The fluorine flow was then stopped and $N_2$ was bubbled through the cold solution for an additional 0.5 hour. The reactor was then allowed to warm in the air to about 20° C. and the liquid contents were transferred to a round bottom flask fitted with a drying tube. The $CFCl_3$ was allowed to distill away until the volume reached about 20 ml. This was then fractioned through a series of four cold traps operated at $-20°$, $-40°$, $-76°$ and $-196°$, C., respectively. The contents of the $-20°$ C. trap were unreacted $CF_3SO_2N(H)CH_3$)3 mmol), the $-40°$ C. trap contained 0.2 mmol of an unidentified imine, probably $CF_3SO_2N=CH_2$, the $-196°$ C. trap contained $CFCl_3$ and the $-76°$ C. trap retained $CF_3SO_2N(F)CH_3$ (4.0 mmol, 11% yield).

N-Fluoro-N-methyl-trifluoromethanesulfonylamide is a colorless liquid with a vapor pressure of 38 torr at 22° C. The infrared spectrum of the gas shows bands at 3011(vw), 2959(vw), 2918(vw), 1443(s), 1425(s), 1230(vs), 1132(s), 1067(w), 1025(m), 917(vw), 884(w), 846(m), 776(w), 683(s) and 602(m) cm$^{-1}$. The $^{19}F$ NMR exhibits resonances at $-40.5$ (quartet, N-F) and $-70.6$ (S,$CF_3$) ppm($CFCl_3$) with $^3J_{HF} = 29$Hz. The $^1H$ NMR shows a resonance at 64.35 (doublet, $CH_3$).

EXAMPLES 3 TO 12

Examples of Fluorinations of Organic Substrates Using $(CF_3SO_2)_2 NF$

EXAMPLE 3

Preparation of diethyl-1-fluoro-1-methylmalonate, $CH_3CF(OC(O)C_2H_5)_2$.

The sodium salt of diethyl-1-methyl malonate was prepared by standard methods. After drying, NaCCH-3($O_2CC_2H_5$)$_2$ (0.238 g, 1.2 mmol) was added to a 25 ml flask and 5 ml of $CCl_4$ was added. This mixture was stirred magnetically and $(CF_3SO_2)_2$ NF (0.36 g, 1.2 mmol) in 5 ml of $CCl_4$ was added dropwise while holding the temperature of the flask at $-10°$ C. After the addition was complete (about 5 minutes) the mixture was stirred for 2 hours. at $-10°$ C. The mixture was then filtered at 22° C. and the filtrate pumped under vacuum to remove solvent. This gave a colorless liquid which by IR and NMR was shown to be pure $CH_3CF(O_2C_2H_5)_2$, (0.225 g, 96% yield). During the reaction, $FN(SO_2CF_3)_2$ is converted to the Na salt $NaN(SO_2CF_3)_2$ which was identical with an authentic sample.

EXAMPLE 4

Preparation of Monofluorotoluene.

By vacuum transfer, $FN(SO_2CF_3)_2$ (1.7 mmol) was added to 2.0 ml of toluene at $-196°$ C. The mixture was warmed to room temperature and agitated by hand. A slow color change ensues near 22° C. After 10 hours, $^{19}F$ NMR shows the presence of 2-fluorotoluene (74%), 3-fluorotoluene (4%) and 4-fluorotoluene (21%). The ratio of unreacted $FN(SO_2CF )_3)_2$ to the $HN(SO_2CF_3)_2$ formed in the reaction indicates an 80% conversion to the monofluorotoluene isomers. No other fluorine containing products are observed by NMR. Example 5

Preparation of Monofluorobenzene

The reaction was carried out in a 5 mm NMR tube for ease of monitoring the reaction products A 0.4 ml sample of benzene was added to the NMR tube at $-196°$ C. by vacuum transfer, followed by 0.5 mmol of $(CF_3SO_2)_2NF$. The tube was sealed and warmed to 22° C. After 3 hours at 22° C., a color change was observed and $^{19}F$ NMR indicated a slow reaction was occuring.

After 18 hours at 22° C., 19F NMR utilizing an internal CFCl$_3$ standard indicated a 50% conversion to monofluorobenzene and HN(SO$_2$CF$_3$)$_2$, with an equal amount of unreacted FN(SO$_2$CF$_3$)$_2$. No other fluorine containing products could be detected by NMR.

EXAMPLE 6

Monofluorination of 1,3,5(10)estratrien-3ol-17one methyl ether

The fluorination reaction was carried out in a 10 mm NMR tube. To 0.28 mmol of the estratrien methyl ether were added 2.5 ml of CDCl$_3$ by vacuum transfer. The mixture was warmed to room temperature forming a colorless solution. This solution was cooled to $-196°$ C. and 0.28 mmol each of FN(SO$_2$CF$_3$)$_2$ and CFCl$_3$ were added by vacuum transfer. The tube was sealed and warmed to $-74°$ C. and then to 22° C. over a 2 hour period. Near $-65°$ C. the colorless solution began to turn to a pale yellow color. After reaching 22° C. $^{19}$F NMR indicated a quantitative amount of (CF$_3$SO$_2$)$_2$NH was formed. Two other fluorine resonances are observed in the ratio of 1:1 with a total area equal to the internal CFCl$_3$ standard. These resonances at $-140.2$ (m) and $-168.6$ (m) ppm relative to CFCl$_3$ are assignable to an equimolar mixture of the two monofluoro derivatives of the estratrien, 2-fluoro-1,3,5(10)estratrien-3ol-17one methyl ether and 4-fluoro-1,3,5(10)estratrien-3ol-17one methyl ether, respectively.

EXAMPLE 7

Monofluorination of Anisole

The fluorination reaction was carried out in a 10 mm NMR tube. Anisole (1.0 mmol) and 2.5 ml of CDCl$_3$ were added to the tube at $-196°$ C. by vacuum transfer. The mixture was warmed to 22° C. to form a solution and recooled to $-196°$ C. (CF$_3$SO$_2$)$_2$NF (1.0 mmol) was then added by vacuum transfer, the tube was sealed, and allowed to warm to 22° C. in a small Dewar flask, initially at $-196°$ C. about 3 hours). The tube was then allowed to stand at 22° C. for 7 hours. $^{19}$F NMR using an internal CFCl$_3$ standard showed complete conversion of (CF$_3$SO$_2$)$_2$NF to (CF$_3$SO$_2$)$_2$NH and three additional somewhat broad singlets at $-122.6$ (24%), $-135.4$ (69%) and $-162.2$ (7%). These signals correspond to 4-fluoro-anisole, 2-fluoro-anisole and polyfluorinated anisole (probably tetra or pentafluoro), respectively. The total yield of monofluoro-anisole was at least 90% by NMR.

Attempts to prepare N-fluoro-bis(perfluoro-n-butane sulfonyl amide, (C$_4$F$_9$SO$_2$)$_2$NF as otherwise conducted by the procedures of Examples 1 to 2 were unsuccessful.

Attempts to fluorinate nitrobenzene, as otherwise conducted by the process of Example 4, were unsuccessful.

EXAMPLES 8 to 12

Additional Examples of Fluorinations with

IV

A series of five fluorination reactions were carried out on five different aromatic compounds. Each reaction was carried out in a 10 mm NMR tube by adding 2 mmol of the aromatic and 2.5 ml of CDCl$_3$ After degassing the solution, 1 mmol of (CF$_3$SO$_2$)$_2$NF was added to the tube at $-196°$ C. by vacuum transfer and after sealing, the tube was warmed to 22° C. with stirring. After 10-12 hrs, $^{19}$F NMR showed complete conversion of the IV compound to its N-H derivative and the formation of fluoroaromatics. The aromatic compounds which were fluorinated in these examples and the fluorinated products thereby obtained (in mol %) were as follows:

| Example | Starting Aromatic | Fluorinated Aromatic Products |
|---|---|---|
| 8 | anisole: | 2-fluoroanisole ($\sim$69%), 4-fluoroanisole ($\sim$24%), other ($\sim$7%). |
| 9 | phenol: | 2-fluorophenol ($\sim$50%), 4-fluorophenol ($\sim$30%), other ($\sim$20%). |
| 10 | m-cresol: | 2-fluoro-5-methyl-phenol ($\sim$35%), 4-fluoro-3-methyl-phenol ($\sim$45%), other ($\sim$20%). |
| 11 | p-cresol: | 2-fluoro-4-methyl-phenol ($\sim$80%), other ($\sim$20%). |
| 12 | napthalene: | 1-fluoro-napthalene ($\sim$80%), 2-fluoro-napthalene ($\sim$7%), other ($\sim$13%). |

EXAMPLE 13

Preparation of C$_4$F$_9$SO$_2$N(F)SO$_2$CF$_3$, N-fluoro-Nonafluoro-n-butylsulfonyl-trifluoromethyl-sulfonyl imide.

C$_4$F$_9$SO$_2$N(H)SO$_2$CF$_3$ (4.0 g, 9.3 mmol) was added to a 150 ml stainless steel bomb in a glove box. The bomb was then cooled to $-20°$ C. and evacuated for 0.5 hour. It was then cooled to $-196°$ C. and fluorine (11 mmol) was added by vacuum transfer The bomb was then allowed to warm in the room air to 22° C. and let stand for 24 hours, at which point it was recooled to $-196°$ C. and evacuated to remove unreacted fluorine and any other materials volatile at $-196°$ C. The remaining volatile materials in the bomb were then vacuum transferred to another stainless steel reactor containing sodium fluoride (25 g) and the mixture was allowed to stand for 2 hours at 22° C., followed by fractionation through a series of cold traps at $-40°$, $-100°$ and $-196°$The n-196° C. trap collected $\sim$0.3 mmol of material consisting mainly of CF$_3$SO$_2$F and C$_4$F$_9$SO$_2$F. The $-100°$ C. trap contained a trace of the desired N-F compound and the $-40°$ C. trap retained pure C$_4$F$_9$SO$_2$N(F)SO$_2$CF$_3$ (4.0 g, 8.9 mmol, 96% yield).

C$_4$F$_9$SO$_2$N(F)SO$_2$CF$_3$ is a colorless liquid at 22° C. which forms a crystalline solid on cooling with a melting point of $-56°$ C. The vapor pressure of the liquid at 22° C. is $\sim$3 torr. The liquid compound showed no decomposition on standing for 3 days at 22° C. The infrared spectrum of the gas at $\sim$3 torr shows bands at 1469(s), 1353(m), 1292(w), 1245(vs), 1207(sh), 1151(s), 1132(s), 1026(w), 1009(w), 865(m), 804(m), 771(w), 746(m), 702(w), 639(w), 582(m), 532(w), 497(m) cm$^-$. The $^{19}$F NMR of CF$_3{}^A$SO$_2$N(F)$^X$-SO$_2$CF$_2{}^B$CF$_2{}^C$CF$_2{}^D$CF$_3{}^E$ is as follows (internal CFCl$_3$ standard, 188.3 MHz) X- 32.4 (broad-singlet); A - 72.2 (doublet); B- 106.0 (triplet of octets); C - 120.8 (complex multiplet); D - 126.1 (complex multiplet); E - 81.1 (ordered 27 line multiplet due to 3 different triplet splittings) with J$_{AX}$=5.0 Hz and the other coupling constants not readily assigned. The integrated areas of all NMR signals were as expected. The mass spectrum shows a weak parent ion under CI with methane at 450 amu (MH+). The EI spectrum shows intense peaks at 69 ($CF_3^+$), 131 ($C_3F_5^+$) and 219 ($C_4F_9^+$) with weak peaks 133 ($CF_3SO_2^+$) and 283 ($C_4F_9SO_2^+$).

EXAMPLE 14

Preparation of $C_6F_{13}SO_2N(F)SO_2CF_3$, N-fluoro-Tridecafluoro-n-hexylsulfonyl-trifluoromethylsulfonyl imide.

$C_6F_{13}SO_2N(H)SO_2CF_3$ (2.4 g, 4.5 mmol) was added to a 75 ml stainless steel bomb in a glove box. The bomb was then cooled to $-20°$ C. and evacuated for 1.0 hour. It was then cooled to $-196°$ C. and fluorine (5.5 mmol) was added by vacuum transfer. The bomb was then allowed to warm in the room air to $22°$ C. and let stand for 4 days, at which point it was recooled to $-196°$ C. and evacuated to remove unreacted fluorine and any other materials volatile at $-196°$ C. The remaining volatile materials in the bomb were then vacuum transferred to another stainless steel reactor containing sodium fluoride (25 g) and the mixture was allowed to stand for 2 hours at $22°$ C., followed by fractionation through a series of cold traps at $-40°$ and $-196°$ C. The $-196°$ C. trap collected a small amount of material consisting mainly of $CF_3SO_2F$ and $C_6F_{13}SO_2F$. The $-40°$ C. trap retained pure $C_6F_{13}SO_2N(F)SO_2CF_3$ (2.3 g, 4.2 mmol, 93% yield).

$C_6F_{13}SO_2N(F)SO_2CF_3$ is a colorless liquid at $22°$ C. which forms a crystalline solid on cooling with a melting point of $-28°$ C. to $-30°$ C. The vapor pressure of the liquid at $22°$ C. is $\sim 1$ torr. The liquid compound showed no decomposition on standing for 3 days at $22°$ C. The infrared spectrum of the gas at $\sim 1$ torr shows bands at 1464(s), 1359(w), 1232(vs), 1151(s), 1127(s), 1045(w), 1021(w), 987(m) 937(w), 889(m), 853(m), 772(w), 744(w), 728(w), 705(w), 683(w), 638(w), 583(m), 492(m) cm$^{-1}$. The $^{19}$NMR of $CF_3^A SO_2N(F)^X SO_2CF_2^B CF_2^C CF_2^D CF_2^E CF_2^F CF_3^G$ is as follows (internal $CFCl_3$ standard, 84.25 MHz) X - 32.4 (broad-singlet); A - 72.2 (singlet); B - 105.8 (triplet); C - 119.7 (multiplet); D - 121.9 (multiplet); E - 122.0 (multiplet), F - 126.6 (multiplet); G - 81.3 (triplet) with coupling constants not readily assigned. The integrated areas of all NMR signals were as expected. The mass spectrum shows a weak parent ion under CI with methane at 550 amu (MH$^+$) with additional intense ions at 485(M$^+$-SO$_2$), 383($C_6F_{13}SO_2^+$), 319($C_6F_{13}^+$), 297($C_4F_9SO_2N^+$), 269($C_5F_{11}^+$), 231($C_5F_9^+$), 181($C_4F_7^+$), 169($C_3F_7^+$), 133($C_3SO_2^+$), 131($C_3F_5^+$), 119($C_2F_5^+$) and 100($C_2F_4^{30}$). The EI spectrum shows intense peaks at 69($CF_3^+$), 100($C_2F_4^+$), 119($C_2F_5^{30}$), 131($C_3F_5^+$), 169($C_3F_7^+$), 181($C_4F_7^+$), 231($C_5F_9^+$), 319($C_6F_{13}^+$).

EXAMPLES 15 and 16

Examples of Fluorinations with $R_fSO_2N(F)SO_2CF_3$ wherein $R_2 = C_4F_9$ and $C_6F_{13}$ The fluorination of toluene was carried out, separately, with each of compounds VII and VIII in a similar manner to that employed in Example 4 above. 1 mmol of toluene, 0.8 mmol of $CFCl_3$ and 0.8 mL of $CDCl_3$ were added to a 5 mm NMR tube. The mixture was cooled to $-196°$ C. and 0.5 mmol of the $R_fSO_2N(F)SO_2CF_3$ compound was then added by vacuum transfer and after sealing the tube, the mixture was warmed to $22°$ C. with shaking. Progress of the reaction was monitored by $^{19}$F NMR. After 24 hours, the VII and VIII compounds were completely converted to the corresponding acids with the formation 2-fluorotoluene (74%), 3-fluorotoluene (trace), 4-fluorotoluene (20%) and an unidentified compound (5%). The use of each of the VII and VIII compounds gave approximately the same results in this regard. Under identical conditions, $(CF_3SO_2)_2NF$ gave essentially the same results except that the reaction clearly proceeded at a faster rate.

EXAMPLES 17 and 18

Examples of Fluorinations with $R_fSO_2N(F)SO_2CF_3$ where $R_f = C_4F_9$ and $C_6F_{13}$.

Preparation of diethyl-1-fluoro-1-methyl malonate, $CH_3CF(OC(O)C_2H_5)_2$.

In an almost identical manner to Example 3 in which $(CF_3SO_2)_2NF$ was used as the fluorinating agent, the sodium salt of diethyl-1-methyl malonate was fluorinated with each of Compounds VII and VIII in dichloromethane. The product was easier to isolate pure from dichloromethane than from carbon tetrachloride. After reaction and workup, the isolated yield of $CH_3CF(OC(O)C_2H_5)_2$ was 94% in each case.

EXAMPLE 19

Preparation of perfluoro-1,3,2-dithiazolidine-1,1,3,3-tetraoxide (Compound IVA)

Compound XIIIB (1.91 g, 7.86 mmol) was added to a 75 ml stainless bomb in a glove box. The bomb was then cooled to $-196°$ C., evacuated, and fluorine (8.6 mmol) was added by vacuum transfer. The bomb was then placed in a cold bath at $-145°$ C. and allowed to warm slowly to $-20°$ C. over 12 hours. It was then warmed to $22°$ C. and allowed to stand for 24 hours. The bomb was then recooled to $-196°$ C. and evacuated to remove unreacted fluorine and any other materials volatile at $-196°$ C. The bomb was then warmed to $-50°$ C. and hydrogen fluoride produced in the reaction along with any other compounds volatile at this temperature were removed under vacuum. The remaining contents of the bomb were then fractionated through cold traps at $-45°$ and $-196°$ C. The compound IVA (1.58 g, 6.05 mmol, 77%) collected in the $-45°$ C. trap and only a trace of material was observed in the $-196°$ C. trap.

Compound IVA is a white crystalline solid at $22°$ C., which sublimes readily under vacuum at $31°-33°$ C. The vapor pressure of the solid at $22°$ C. is 13 torr. The compound shows no decomposition on standing for 3 days at $22°$ C. The infrared spectrum of the gas at 10 torr shows bands at 1463(s), 1279(s), 1224(vs), 1163(m), 965(m), 927(s), 750(s), 712(s), 626(m), 559(m), 484(m), 314(w) cm$^{-1}$. The $^{19}$F NMR ($CDCl_3$ solvent, $CFCl_3$ internal standard, 84.25 MHz) consists of singlets at $-104.5$ ($CF_2$) and $-13.9$(N-F) in the ratio of 4:1. The mass spectrum shows a moderately intense parent ion under CI with methane at 262 amu (MH$^+$). The EI spectrum shows a very intense peak at 100 ($C_2F_4^+$) with additional very intense peaks at 200(?) and 100($C_2F_4^+$) with aditional moderately intense peaks at 81($C_2F_3^+$), 69($CF_3^+$), 64($SO_2^+$) and 48($SO^+$).

EXAMPLE 20

Preparation of 2,4,4,5,5,6,6,-heptafluoro-dihydro-1,3,2-dithiazine-1,1,3,3,-tetraoxide(compound IVB)

Compound XIIIC (1.36 g, 4.6 mmol) was added to a 75 ml stainless bomb in a glove box. The bomb was then cooled to −196° C., evacuated, and fluorine (5.1 mmol) was added by vacuum transfer. The bomb was then placed in a cold bath at −145° C. and allowed to warm slowly to −20° C. over 12 hours. It was then warmed to 22° C. and allowed to stand for 24 hours. The bomb was then recooled to −196° C. and evacuated to remove unreacted fluorine and any other materials volatile at −196° C. The bomb was then warmed to −50° C. and hydrogen fluoride produced in the reaction along with any other compounds volatile at this temperature were removed under vacuum. The remaining contents of the bomb were then fractionated through cold traps at −40° and −196° C. Compound IVB (0.87 g, 2.8 mmol, 61%) collected in the −40° C. trap and only a trace of material was observed in the −196° C. trap.

Compound IVB is a white crystalline solid at 22° C., which sublimes readily under vacuum at 42°–45° C. The vapor pressure of the solid at 22° C. is ~8 torr. The compound shows no decomposition on standing for 3 days at 22° C. The infrared spectrum of the gas at ~8 torr shows bands at 1475(vs), 1287(w,sh), 1263(w,sh), 1207(vs), 1165(m), 1063(w), 1026(s), 994(m), 922(s), 814(m), 698(w), 655(w), 630(m), 575(w), 524(m), 466(w) cm$^{-1}$. The $^{19}$F NMR (CDCl$_3$ solvent, CFCl$_3$ internal standard, 84.25 MHz) consists of a singlet at −27.2 (N-F) and a second order multiplet consisting of 7 major lines at −101.6, −104.9, −114.4, −117.4, −128.4, −130.8 and −134.0 (—CF$_2$—CF$_2$—CF$_2$—) with integrated intensities of N-F to C-F of 1:6. The mass spectrum shows a very intense parent ion under CI with methane at 312 amu(MH$_+$) with an additional intense ion at 100 (C$_2$F$_4$+). The EI spectrum shows a very intense peak at 100 (C$_2$F$_4$+) with additional intense peaks at 131(C$_3$F$_5$+), 69(CF$_3$+) (SO$_2$+) and 48(SO+).

EXAMPLES 21 and 22

Examples of Fluorinations with Compounds IVA and IVB

The fluorination of benzene was carried out in a manner similar to that employed in Examples 15 and 16. 0.2 mmoles of each of compounds IVA and IVB were separately combined with 1 mmol of benzene in CDCl$_3$/CFCl$_3$ solvent. After 12 hrs, $^{19}$F NMR showed the formation of monofluorobenzene and the respective N-H compound along with unreacted N-F compound in each reaction. Based on the amount of unreacted N-F compound there was a 42% conversion to monofluorobenzene and the respective acids in each case.

What is claimed is:

1. A compound of the formulae

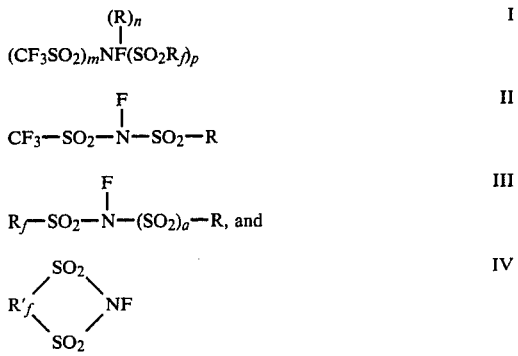

wherein
R is a hydrocarbon radical which is substituted or is unsubstituted and which is a C$_{1-30}$ branched or straight chain alkyl, C$_{3-30}$ cycloalkyl, or aryl (C$_{1-10}$ alkyl) or aryl group wherein aryl and aryl are C$_{6-14}$ arylene,
R$_f$ is a perfluorinated radical which is C$_{2-30}$ branched or straight chain alkyl, C$_{3-30}$ cycloalkyl, or aryl (C$_{1-10}$ alkyl) or aryl group wherein aryl and aryl are C$_{6-14}$ arylene,
R'$_f$ is a perfluorinated radical which is (CF$_2$)$_{n'}$ wherein n' is 1 to 4,
a is 0 or 1 and
m is 1 or 2, n is 0 or 1, p is 0 or 1 and m+n+p=2.
2. A compound as in claim 1 which has formula I.
3. A compound as in claim 1 which has formula II.
4. A compound as in claim 1 which has formula III.
5. A compound as in claim 1 which has formula IV.
6. A compound as in claim 2 which has the formula (CF$_3$SO$_2$)$_m$ NF(R)$_n$.
7. A compound as in claim 6 which has the formula (CF$_3$SO$_2$)$_2$NF).
8. A compound as in claim 6 which has the formula (CF$_3$SO$_2$)N(F)R.
9. A compound as in claim 8 in which R is a C$_{1-30}$ alkyl group.
10. A compound as in claim 9 which has the formula (CF$_3$SO$_2$)N(F)(CH$_3$).

11. A compound as in claim 2 which has the formula (CF$_3$SO$_2$)NF(R$_f$SO$_2$).

12. A compound as in claim 11 in which R$_f$ is a C$_{1-30}$ alkyl group.
13. A compound as in claim 12 in which R$_f$ is C$_4$F$_9$.
14. A compound as in claim 12 in which R$_f$ is C$_6$F$_{13}$.
15. A compound as in claim 5 in which n' is 2.
16. A compound as in claim 5 in which n' is 3.

* * * * *